(12) United States Patent
Paananen et al.

(10) Patent No.: US 6,770,757 B2
(45) Date of Patent: Aug. 3, 2004

(54) METHOD FOR RECOVERING PRODUCTS FROM PROCESS SOLUTIONS

(75) Inventors: Hannu Paananen, Kantvlk (FI); Jarmo Kuisma, Lohja as (FI); Vili Ravanko, Kirkkonummi (FI); Nina Mayra, Helsinki (FI); Heikki Heikkila, Espoo (FI); Jari Lewandowski, Kirkkonummi (FI)

(73) Assignee: Finnfeeds Finland Oy, Espoo (FI)

( * ) Notice: Subject to any disclaimer, the term of this patent is extended or adjusted under 35 U.S.C. 154(b) by 0 days.

(21) Appl. No.: 09/967,183

(22) Filed: Sep. 28, 2001

(65) Prior Publication Data

US 2002/0169311 A1 Nov. 14, 2002

(30) Foreign Application Priority Data

Sep. 29, 2000 (FI) .............................. 2001-2150

(51) Int. Cl.[7] .......................... C07G 17/00; C07H 1/00; C13J 1/06; B01D 15/08
(52) U.S. Cl. .................. 536/127; 536/124; 127/42; 127/46.1; 127/46.2; 210/635; 210/659; 210/656
(58) Field of Search ................. 210/635, 659, 210/656; 127/42, 46.1, 46.2; 536/124, 127

(56) References Cited

U.S. PATENT DOCUMENTS

| 4,333,770 A | | 6/1982 | Neuzil et al. |
| 4,358,322 A | | 11/1982 | Neuzil et al. |
| 4,359,430 A | * | 11/1982 | Heikkila et al. |
| 4,405,377 A | | 9/1983 | Neuzil |
| 4,405,378 A | | 9/1983 | Kulprathipanja |
| 5,127,957 A | | 7/1992 | Heikkila et al. |
| 5,998,607 A | | 12/1999 | Heikkila et al. |
| 6,093,326 A | * | 7/2000 | Heikkila et al. |
| 6,224,776 B1 | * | 5/2001 | Heikkila et al. |

FOREIGN PATENT DOCUMENTS

| CN | 1234404 A | * | 11/1999 |
| JP | 39-5429 | | 4/1964 |
| JP | 39-5429 | | 5/1997 |
| WO | WO 94/17213 | | 8/1994 |
| WO | WO 98/53089 | | 11/1998 |

OTHER PUBLICATIONS

1. Journal of Chromatography, 256 (1983) pp. 157–163.
3. Sayama, Kouji, et al. Proc. Res. Soc. Japan Sugar Refineries Technol., 198, vol. 29, 1–27.
4. McCready, R.M. et al.,Journal of the A.S>S.B.T., vol. 14, No. 2, Jul. 1966, pp. 127–132.

* cited by examiner

Primary Examiner—James O. Wilson
Assistant Examiner—Traviss C. McIntosh, III
(74) Attorney, Agent, or Firm—Scully, Scott, Murphy & Presser

(57) ABSTRACT

The invention relates to a method comprising a multistep process for recovering betaine, erythritol, inositol, sucrose, mannitol, glycerol and amino acids from corresponding starting materials. The invention comprises the use of a weakly acid cation exchange resin in chromatographic column in the multistep process. The starting materials are especially beet molasses, betaine molasses, syrups, thick juices, raw juices, corn steep cane based solutions and glycerol.

44 Claims, 5 Drawing Sheets

Example 1.

Example 2.

Example 3.

METHOD FOR RECOVERING PRODUCTS FROM PROCESS SOLUTIONS

FIELD OF THE INVENTION

The present invention relates to a method comprising a multistep process recovering betaine, erythritol, inositol, sucrose, mannitol, glycerol and amino acids from corresponding starting materials by using a weakly acid cation exchange resin in a column. More particularly, the present invention relates to the use of a weakly acid cation exchange resin in a chromatographic column in a method for multistep process for recovering products from solutions obtained from the processing of beet derived solutions, such as beet molasses, betaine molasses and vinasse. The corresponding starting materials are especially beet molasses, betaine molasses, cane molasses, syrups, thick juices, raw juices, corn steep and cane based solutions.

BACKGROUND OF THE INVENTION

Chromatographic separation has been used for recovering betaine, inositol and sucrose from natural materials such as beet molasses, betaine molasses and vinasse. The resins most commonly used in the known chromatographic separations have been strongly acid cation exchangers, i.e. sulfonated polystyrene cross-linked from 3.5 to 8% by weight with divinyl benzene, the resin being in monovalent or divalent form. However, the separation of inositol by using strongly acid cation exchange resins has turned out to be difficult. There is no experience of separating erythritol and mannitol from beet derived solutions. Water is generally a preferred eluant, but the problem when using water is that the various products, such as betaine, erythritol, inositol, sucrose, mannitol, amino acids and mixtures of amino acids have similar retention times, whereby the fractions will overlap.

Publication WO 94/17213 describes a process for fractioning molasses using a chromatographic simulated moving bed system. The product or the products are collected during a multistep sequence comprising the steps of feeding molasses, elution and recycling. Fractionation of molasses denotes fractionation of various vegetable derived by-products of the food and fermenting industries, such as beet and cane molasses, stillage, vinasse, slop, wood molasses, corn steep liquor, wheat, barley and corn molasses (hydrolyzed C-starch). Strongly acid cation exchange resin were preferably used as the chromatographic column packing material, the resins used in the examples had a polystyrene/divinylbenzene backbone and were activated with sulphonic acid groups. The resin was preferably in monovalent form such as sodium or potassium or as a mixture of these forms. The products of the process comprised residue and sucrose and/or betaine.

WO 98/53089 describes a process for the simultaneous obtaining of converted and non-converted sugar and/or non-sugar products, especially isomaltulose and/or trehalulose and betaine or invert sugar from plant derived solutions. The sucrose containing solution is subjected to transglucosylation and in the next phase recovering from said transglucosylated solution isomaltulose and/or trehalulose and non-converted sugar and/or non-sugar products by a process including separate chromatographic recovery. A strong acid cation exchange resin cross-linked with DVB in $Na^+$ form was used.

DE 2 232 093 discloses a process for separating sugars from molasses by using ion-exclusion resins. Eluant used in the process is water and sugar containing solution. The eluant is recycled back to the process. Low purity fractions are also used for reviving the resin. Strong acid cation exchange resin is mentioned in the examples.

Japanese patent publication No. 39-5429 describes a process for separating betaine from sugar containing liquid especially sugar beet derived, by ion exchange resin. In the process betaine is separated by using strong acid cation exchange resin in $Na^+$ form by eluting it with water without any regenerants.

DE 2 362 211 describes a method for separating sugars from molasses by liquid chromatography. A cation exchanger in $Ca^{2+}$ form is used in the method. Erythritol, inositol and mannitol have not been mentioned in the patent, neither does it suggest fractioning of betaine. In the examples a strong acid cation exchange resin is used.

U.S. Pat. No. 4,359,430 discloses a process for recovering betaine from molasses by using a chromatographic column of a salt of a polystyrene sulphonate cation exchange resin cross coupled with DVB, and eluting with water. The first fraction separated is a waste fraction and the second fraction contains a substantial proportion of the sugars of the feed solution, the third fraction consists principally of betaine.

Munir, M., (Zucker 28 (1975) No. 6 pp. 286–294) has described a desugarization of molasses by means of liquid distribution chromatography. In the article betaine is mentioned but not sugar alditols, and even though the betaine is mentioned it has not been suggested that betaine should be recovered. The strong acid cation exchange resin is used in $Ca^{2+}$ form.

From U.S. Pat. No. 5,127,957 is known a method wherein betaine is separated from beet molasses using a chromatographic simulated moving bed system having at least three chromatographic columns connected in series. Strong acid cation exchange resins were used where the resin contained sulphonic acid groups. The resin was regenerated into sodium form.

U.S. Pat. No. 4,358,322 discloses a process for separating fructose from a feed mixture comprising fructose and glucose. The process comprises contacting the mixtures with an adsorbent comprising aluminosilicate or zeolite. The adsorbent contains one or more selected cations at exchangeable cations sites. The cations are selected from the group consisting of sodium, barium and strontium. The cationic pairs used in the cationic sites are selected from the groups consisting of barium and potassium and barium and strontium.

From U.S. Pat. No. 4,405,377 is known a process for the separation of a monosaccharide from at least one other monosaccharide. The aqueous feed solution of the monosaccharides is diluted with ethanol and contacted with an adsorbent comprising a crystalline aluminosilicate. The crystalline aluminosilicate is selected from X zeolites and Y zeolites.

From U.S. Pat. No. 4,333,770 is known that various sugars and particularly sucrose may be separated from mixtures of sugars including glucose, fructose, raffinose etc. by treating an aqueous solution of the molasses with an adsorbent which will selectively adsorb sucrose thereon. The adsorbent comprises a shaped replication of inorganic support particle aggregates. The adsorbent consists of a carbonaceous pyropolymer containing at least carbon and hydrogen atoms. Alcohol solutions are used as eluents. The preferred alcohols contain methanol and ethanol.

From U.S. Pat. No. 4,405,378 is known a process for separating sucrose from aqueous solutions containing sucrose and betaine and mineral salts. The feed solution is contacted with an adsorbent which comprises activated carbon powder bound with a binder material. The binder material consists essentially of a water permeable organic polymer selected from the group consisting of cellulose nitrate, a cellulose ester and a mixture of a cellulose nitrate and cellulose ester. The sucrose is removed from the adsorbent by treatment with a desorbent material comprising a water and methanol mixture. It has not been possible to separate betaine from the mineral salts, only the separation of sucrose is possible.

Kouji Sayama et al. (Proc. Res. Soc. Japan Sugar Refineries Technol. 1980, vol 29, 1–27) describe recovery of sucrose from molasses using a strongly acid cation exchange resin in sodium form. They also describe separation of betaine and recovery of inositol from molasses by using a strongly acid cation exchange resin in $Ca^{2+}$ form.

McCready, R. M. et al (1965) describe the preparation of galactinol and myoinositol from sugar beet syrup by chromatography on a cation exchange resin. A strongly acid cation exchange resin in potassium form was used for separation of myoinositol and galactinol. Water was used as eluant.

It has surprisingly been found that when using in a multistep process a weakly acid cation exchange resin, products can be recovered from solutions obtained from the processing of e.g. beet molasses, betaine molasses and vinasse. The order of elution of valuable carbohydrates in the chromatographic column is different from that previously known. An additional feature is that the elution order of components with the weakly acid cation exchange resin seems to be affected strongly by the hydrophobic/hydrophilic interaction of the component of the product with the resin and this can be used advantageously in the multistep process. In the chromatographic column other features are preferably e.g. ion exclusion and size exclusion. Other process steps used in the multistep process are e.g. crystallization, evaporation, ion exchange and filtration. It seems that if the resin is in hydrophilic form, the most hydrophobic monosaccharide is eluted first and the most hydrophilic last. This results in a clearly different order of separation than when used a strongly acid cation exchange. This is especially advantageous when fractioning a multicomponent solutions.

SUMMARY OF THE INVENTION

The above mentioned objects and others are accomplished by the present invention, which relates to a multistep process for recovering one or more products from a solution containing betaine, erythritol, inositol, sucrose, mannitol, glycerol, amino acids and mixtures thereof by using chromatographic separation comprising at least one step, where a weakly acid cation exchange resin is used in at least one chromatographic column for the chromatographic separation.

BRIEF DESCRIPTION OF THE DRAWINGS

The following drawings are illustrative embodiments of the invention and are not meant to limit the scope of the invention as defined in the claims.

DETAILED DESCRIPTION OF THE INVENTION

Figure 1:
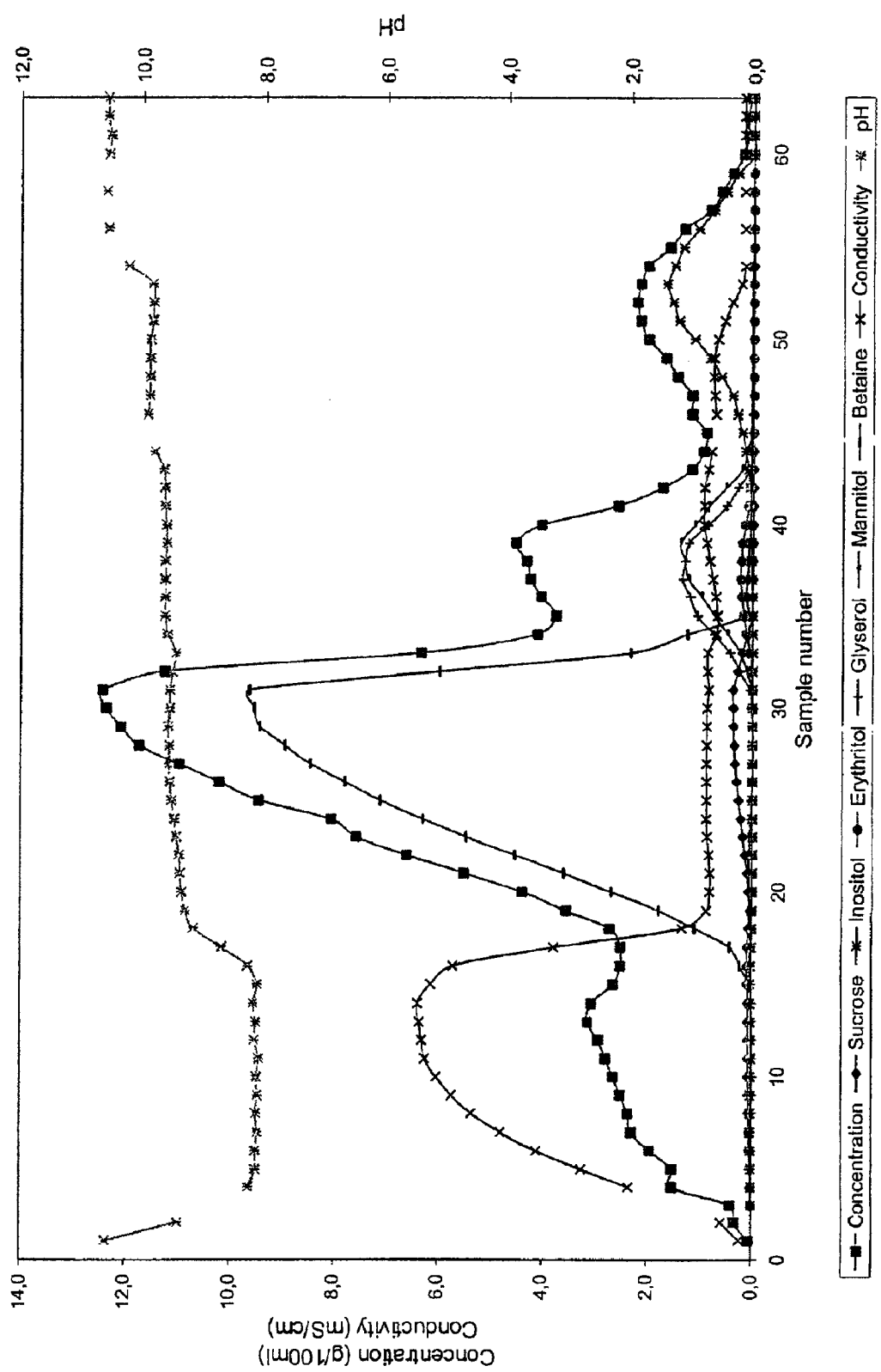
FIG. 1 is a graphical presentation of the elution profiles and pH according to Example 1.

According to the present invention, a multistep process is used where at least in one chromatographic separation step a weakly acid cation exchange resin is used. Further according to the present invention a solution obtained from the processing of e.g. sugar beet derived molasses, betaine molasses and vinasse is subjected to chromatographic separation. Suitable products to be recovered by the method of the present invention are e.g. those selected from the group consisting of e.g. betaine, amino acids, erythritol, inositol, mannitol, glycerol and sucrose and mixtures thereof. It seems that if the resin is in hydrophilic form the most hydrophobic product is eluted first and the most hydrophilic product is eluted last.

Other steps in the multistep process may be chromatographic separation using a strongly acid cation exchange resin, crystallization, evaporation, ion exchange, filtration, precipitation, or some other known process unit.

The chromatographic column or a part of the column used in the method of the present invention is filled with a weakly acid cation exchange resin, preferably an acrylic cation exchange resin having carboxylic functional groups. Such an acrylic resin is preferably derived from methyl acrylate, ethyl acrylate, buthyl acrylate, methylmethacrylate or acrylonitrile or acrylic acids or mixtures thereof. The resin may be crosslinked with a crosslinking agent, e.g. divinyl benzene (DVB). A suitable crosslinking degree is 1 to 20%, preferably 3 to 8%. The average particle size of the resin is normally 10 to 2000 $\mu$m, preferably 100 to 400 $\mu$m. The resin may be regenerated into $H^+$, $Na^+$, $K^+$, $Mg^{2+}$ or $Ca^{2+}$ form. However, also other ionic forms may be used.

The column is preferably eluted at temperatures from 10 to 95° C., more preferably from 30 to 95° C., more preferably from 65 to 95° C. It is known that a higher separation temperature decreases the viscosity and improves the separation performance.

The eluant used in the chromatographic separation according to the present invention is preferably water.

The process solution to be fractioned is optionally pretreated before chromatographic separation by filtration, which can be carried out by using a pressure filter and diatomaceous earth as a filter aid. The pH of the feed solution is optionally adjusted to 6–11, preferably to 9–11. For instance when pH is high, i.e. over 7, betaine is eluted before e.g. inositol and mannitol. After the pH has been adjusted the solution may be filtered. Prior to the chromatographic separation the dry substance of the feed solution is adjusted to an appropriate level.

A feeding device is used for feeding the solution to the column. The temperature of the column, feed solution and eluant is most preferably approximately from 65 to 95° C. This is accomplished by preheating the feed solution. The feed solution is eluted in the column by feeding water, for instance demineralized water or condensate water or some other aqueous solution into the column. Preferably preheated eluant is used. The flow rate in the column is adjusted to an appropriate level. The fractions of the outcoming solutions are collected at suitable intervals and analyzed. The out-flow from the column may be monitored by on-line instruments. The fractionated products, e.g. betaine, erythritol, mannitol and inositol, may be isolated by crystallization.

Crystallization, evaporation and filtration can also be used as separation units as well as other well known process units for separating multicomponent solutions. Further, it is possible to arrange two or more chromatographic columns in sequence wherein at least one column or a part of the column contains a weakly acid cation exchange resin, the other columns possibly containing a strongly acid cation exchange resin. The chromatographic system used can be either batch process or simulated moving bed system. The simulated moving bed system can be either continuous or sequential. In a preferred embodiment of the invention a first column containing strongly acid cation exchange resin is connected to a second column containing a weakly acid cation exchange resin. Such an arrangement further improves the separation performance and increases the yields and purity of the products. The yield of betaine is also improved by removing the side products from the process.

It is also possible to connect two chromatographic columns or part of the columns containing weakly acid cation exchange resin to each other by some other process units. The process units can be for example filtration, pH-adjustment or concentration by evaporation. It is obvious for a person skilled in the art that the order of the process units may be selected and varied. Some examples of the possible process unit flow schemes are show in FIG. 5. These examples are not to be construed to limit the claims in any manner whatsoever.

Figure 5:
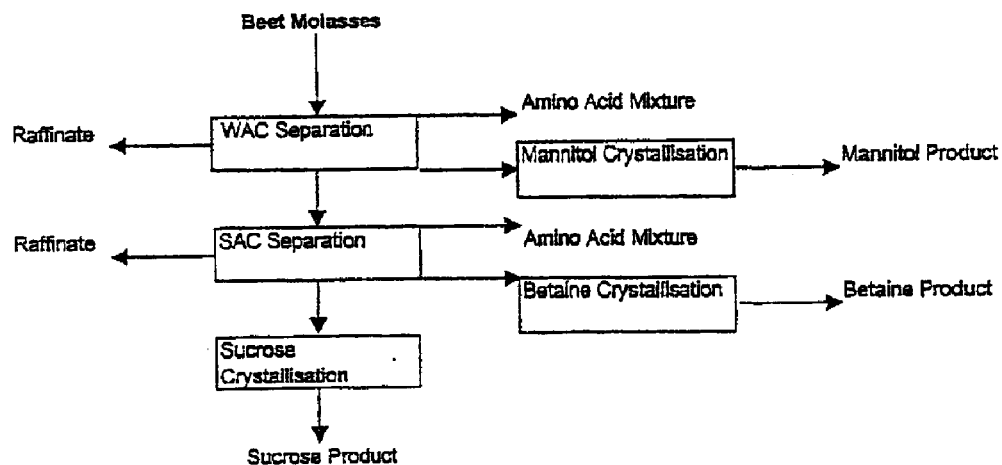
FIG. 5 is a graphical presentation of some possibilities to unite different process units.
Figure 5:
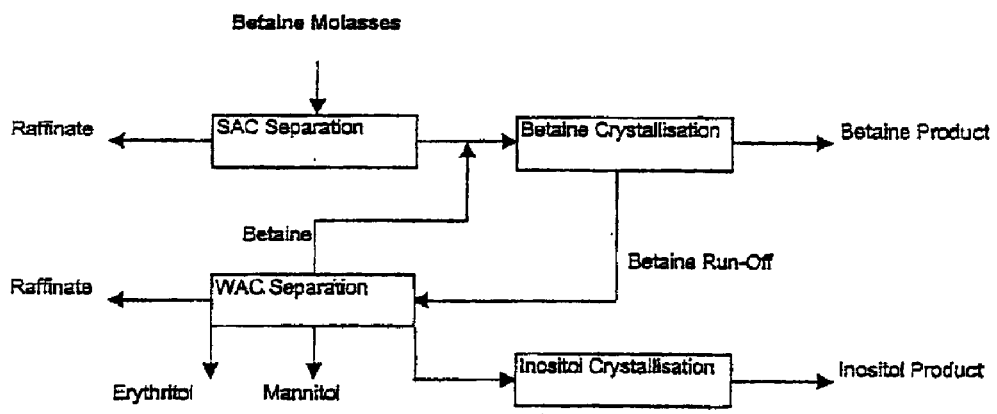
Figure 5:
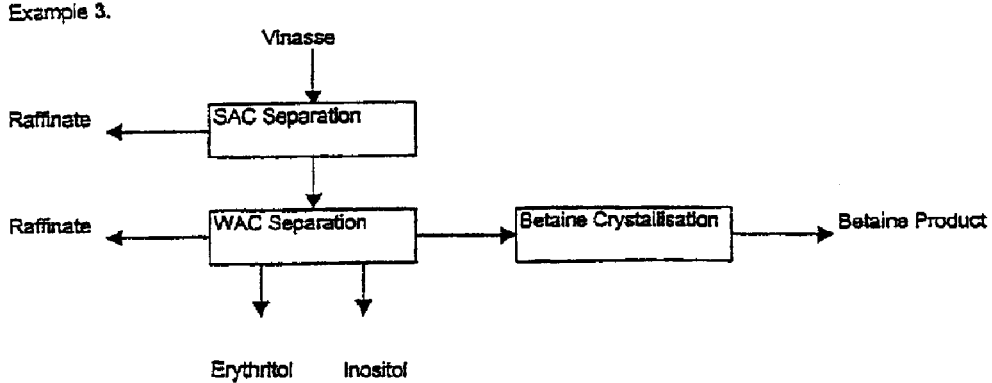

Example 1 in FIG. 5 shows a separation process for beet molasses. Raffinate, sucrose, betaine, amino acid mixture and/or mannitol fractions are collected in the first step using a weakly acid cation exchange resin. Amino acids and/or mannitol fractions may be crystallized. Sucrose-betaine fraction is separated in the next step with a strong acid cation exchange resin to produce raffinate, sucrose and betaine. Amino acids may be collected during this step also. Sucrose and betaine may be crystallized.

Example 2 in FIG. 5 presents a process for betaine molasses separation. The first step uses a strong acid cation exchange resin to separate raffinate and betaine fractions. Betaine can be crystallized and the betaine run-off separated in the second step with a weakly acid cation exchange resin. Raffinate, erythritol, mannitol, betaine and inositol may be collected. Purified inositol can also be crystallized.

In Example 3 in FIG. 5 vinasse is separated first by using a strong acid cation exchange resin. Raffinate and betaine fractions are collected. The betaine fraction is further separated with a weakly acid cation exchange resin to produce raffinate, erythritol, inositol and betaine.

In the multistep process the order of elution of separated components in chromatographic column in the present invention is advantageously different from the order obtained by the earlier methods e.g. based on using strongly acid cation exchange resins and this feature can be advantageously used in the multistep process. According to the present invention betaine is eluted before erythritol, mannitol and inositol. This allows them to be recovered in good yields with high purity in the multistep process of the invention.

The method according to the present invention makes it possible to separate and recover products, such as betaine, erythritol, inositol, mannitol, glycerol, sucrose, amino acids and mixtures of amino acids in good yields from process solutions, which has been very difficult by known methods using e.g. strongly acid cation exchange resins, zeolites or pyropolymers. One of the advantages achieved by the method of the present invention over the prior art is that the use of a weakly acid cation exchange resin makes possible effective separation by using water as an eluant. When water is used as the eluant, the handling is easier, the costs are lower and the safety is higher.

One advantage of the method of the present invention is that only one eluant, water, can be used efficiently for different chromatographic steps. The different elution order of separation of carbohydrates gives additional benefit in the method of the present invention using weakly acid cation exchange resin in the chromatographic separation, making it possible to efficiently recover also other components besides carbohydrates, such as betaine and amino acids.

The following examples illustrate the present invention. The examples are not to be construed to limit the claims in any manner whatsoever.

EXAMPLE 1

Chromatographic Separation of Betaine Crystallization Run-Off with a Weakly Acid Cation Exchange Resin Betaine crystallization run-off originated from beet molasses chromatographic separation was subjected to a chromatographic separation. The separation was performed in a laboratory chromatographic separation column as a batch process. The column with a diameter of 0.045 m was filled with an acrylic weakly acid cation exchange resin (Finex CA 12 GC) manufactured by Finex Oy, Finland. The resin was an ethyl acrylate-based resin. The height of the resin bed was about 0.70 m. The cross linkage degree of the resin was 6% DVB and the average particle size of the resin was 0.26 mm. The resin was in $Na^+$-form. The pH of the resin was high after the manufacturing process. A feeding device was placed at the top of the resin bed. The temperature of the column and feed solution and eluant water was approximately 80° C. The flow rate in the column was adjusted to 4 ml/min. The feed solution was filtered via filter by using diatomaceous earth as filter aid. The pH of the feed solution was 8.9.

The chromatographic separation was carried out as follows:

Step 1: The dry substance of the feed solution was adjusted to 25 g dry substance in 100 g solution according to the refractive index (RI) of the solution.

Step 2: 100 ml of preheated feed solution was pumped to the top of the resin bed.

Step 3: The feed solution was eluted downwards in the column by feeding preheated ion-exchanged water to the top of the column.

Step 4: 10 ml samples of the outcoming solution were collected at 3 min intervals. The composition of the samples was analysed with HPLC ($Ca^{2+}$-form resin, 0.6 ml/min, 0.001 M $Ca(NO_3)_2$, 85° C.).

Betaine eluted from the column after salts. Erythritol, mannitol and glyserol had almost similar retention time eluting almost as a one peak after betaine. Inositol eluted last as a separate peak. The elution order of betaine and alditols seems to be consistent with the hydrophobic/hydrophilic-nature of the components. The resin separated betaine and inositol from other components well. The pH of the effluent, the solution coming out of the column is from 8 to 11. The results are shown graphically in FIG. 1.

EXAMPLE 2

Chromatographic Separation of Sodium Chloride, Betaine, Erythritol and Inositol with a $Na^+$-Form Resin A solution containing betaine, erythritol, inositol and sodium chloride (NaCl) was subjected to a chromatographic separation. The solution was prepared by dissolving pure betaine, erythritol, inositol and sodium chloride into demineralized water. The separation was performed in a laboratory chromatographic separation column as a batch process. The column with a diameter of 0.045 m was filled with an acrylic weakly acid cation exchange resin (Finex™ CA 12 GC) manufactured by Finex Oy, Finland. The resin was an ethyl acrylate-based resin. The height of the resin bed was about 0.70 m. The cross-linkage degree of the resin was 6% DVB and the average particle size of the resin was 0.26 mm. The resin was in $Na^+$-form. The pH of the resin was high after the manufacturing process. A feeding device was placed at the top of the resin bed. The temperature of the column and feed solution and eluant water was approximately 80° C. The flow rate in the column was adjusted to 4 ml/min.

The chromatographic separation was carried out as follows:

Step 1: The dry substance of the feed solution was adjusted to 25 g dry substance in 100 g solution according to the refractive index (RI) of the solution. The feed solution composed of 30% on dry substance (DS) betaine, 30% on DS inositol, 30% on DS erythritol and 10% on DS sodium chloride.

Step 2: 100 ml of preheated feed solution was pumped to the top of the resin bed.

Step 3: The feed solution was eluted downwards in the column by feeding preheated ion-exchanged water to the top of the column.

Step 4: 10 ml samples of the outcoming solution were collected at 3 min intervals. The composition of the samples was analysed with HPLC ($Ca^{2+}$-form resin, 0.8 ml/min, 0.001 M $Ca(NO_3)_2$, 85° C.).

Figure 2:
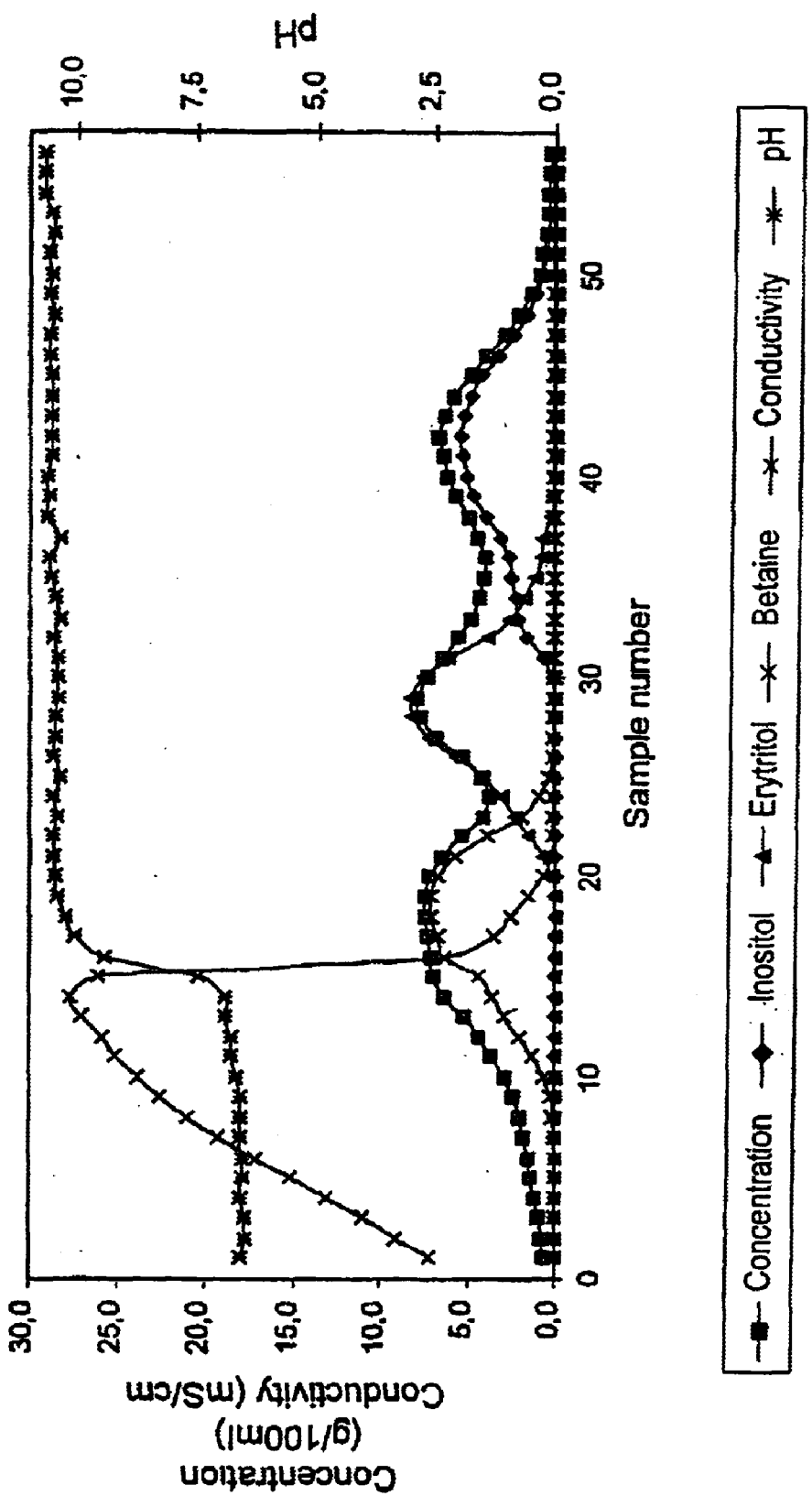
FIG. 2 is a graphical presentation of the elution profiles and pH according to Example 2.

Components were eluted from the column in the following order: sodium chloride, betaine, erythritol and inositol. The elution order of betaine and alditols seems to be consistent with the hydrophobic/hydrophilic-nature of the components. The resin separated components from each other well. The pH of the effluent, the solution coming out of the column is from 6.5 to 11. The results are shown graphically in FIG. 2.

EXAMPLE 3

Chromatographic Separation of Sodium Chloride, Betaine, Sucrose and Mannitol with a $Na^+$-Form Resin A solution containing betaine, sucrose, mannitol and sodium chloride (NaCl) was subjected to a chromatographic separation. The solution was prepared by dissolving pure betaine, sucrose, mannitol and sodium chloride into demineralized water. The separation was performed in a laboratory chromatographic separation column as a batch process. The column with a diameter of 0.045 m was filled with an acrylic weakly acid cation exchange resin (Finex CA 12 GC) manufactured by Finex Oy, Finland. The resin was an ethyl acrylate-based resin. The height of the resin bed was about 0.65 m. The cross-linkage degree of the resin was 6% DVB and the average particle size of the resin was 0.26 mm. The resin was in $Na^+$-form. The pH of the resin was high after the manufacturing process. A feeding device was placed at the top of the resin bed. The temperature of the column and feed solution and eluant water was approximately 80° C. The flow rate in the column was adjusted to 4 ml/min.

The chromatographic separation was carried out as follows:

Step 1: The dry substance of the feed solution was adjusted to 25 g dry substance in 100 g solution according to the refractive index (RI) of the solution. The feed solution composed of 30% on dry substance (DS) betaine, 30% on DS sucrose, 30% on DS mannitol and 10% on DS sodium chloride.

Step 2: 100 ml of preheated feed solution was pumped to the top of the resin bed.

Step 3: The feed solution was eluted downwards in the column by feeding preheated ion-exchanged water to the top of the column.

Step 4: 10 ml samples of the outcoming solution were collected at 3 min intervals. The composition of the samples was analysed with HPLC ($Na^+$-form resin, 0.8 ml/min, 0.003 M $Na_2SO_4$, 85° C.).

Figure 3:
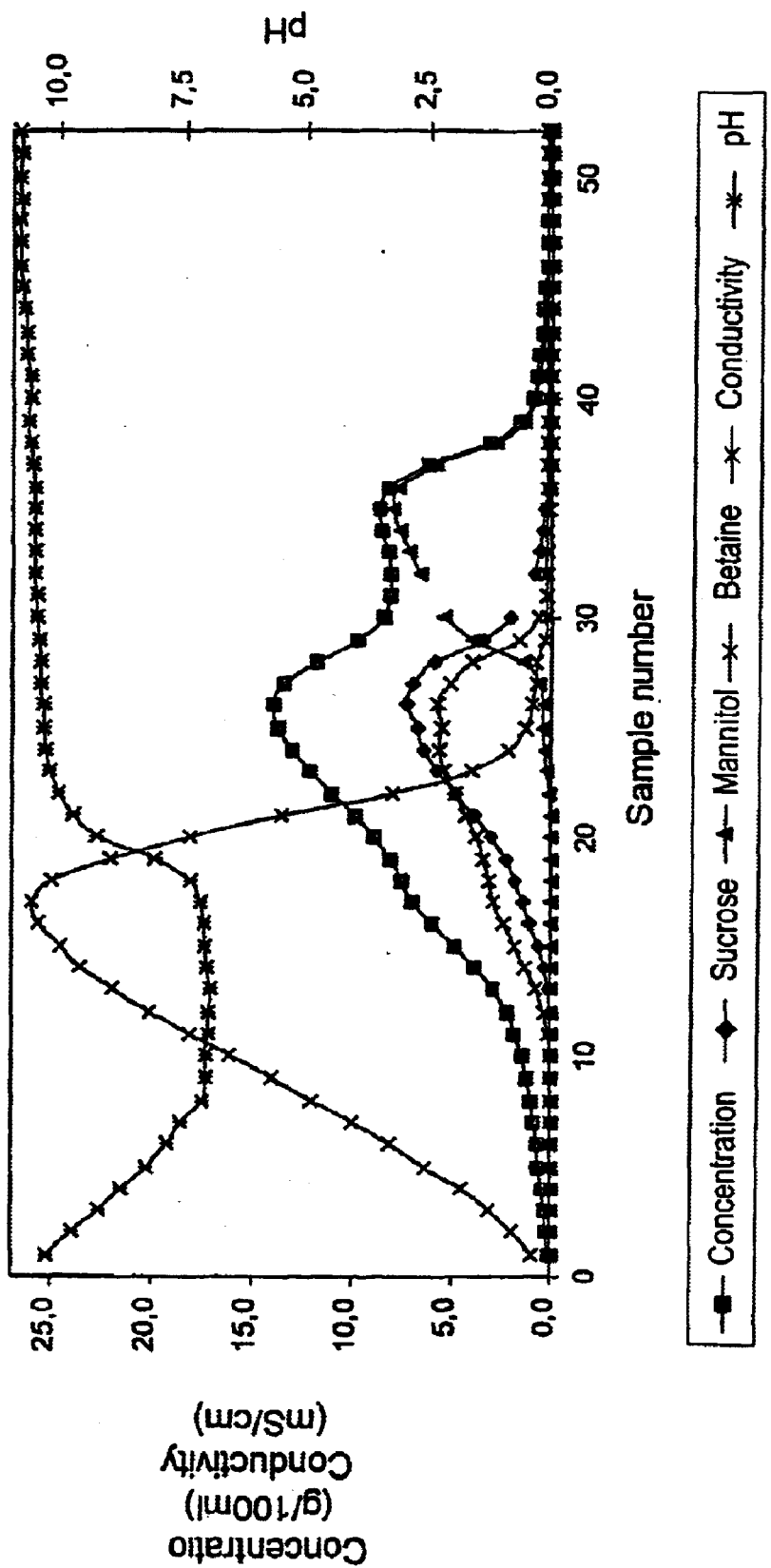
FIG. 3 is a graphical presentation of the elution profiles and pH according to Example 3.

First sodium chloride, sucrose and betaine were eluted from the column together as a one peak. Mannitol was eluted from the column as a separate peak after sucrose and betaine. Resin separated mannitol from sucrose and betaine well. The pH of the effluent, the solution coming out of the column is from 7 to 11. The results are shown graphically in FIG. 3.

EXAMPLE 4

Chromatographic Separation of Beet Molasses with Weakly Acid Cation Exchange Resin Beet molasses was subjected to a chromatographic separation. The separation was performed in a laboratory scale chromatographic separation column as a batch process. The column with a diameter of 0.045 m was filled with an acrylic weakly acid cation exchange resin (Finex™ CA 16 GC, manufactured by Finex Oy, Finland). The resin was methyl acrylate based. The cross-linkage degree of the resin was 8% DVB and the average particle size about 0.23 mm. The resin was in $Na^+$-form prior the separation.

The height of the resin bed was about 0.70 m. The pH of the resin was quite high after the manufacturing process (pH about 9–10). A feeding device was placed at the top of the resin bed. The temperature of the column, feed solution and eluant water was approximately 80° C. The flow rate in the column was adjusted to 4 ml/min. The feed solution was filtered via filter prior the separation. The pH of the feed solution was about 8.2.

The chromatographic separation was carried out as follows:

Step 1: The dry substance of the feed solution was adjusted to 25 g dry substance in 100 g solution according to the refractive index (RI) of the solution.

Step 2: 100 ml of preheated feed solution was pumped to the top of the resin bed.

Step 3: The feed solution was eluted downwards in the column by feeding preheated ion-exchanged water to the top of the column.

Step 4: 10 ml samples of the outcoming solution were collected in 3 min interval. The composition of the samples was analysed with HPLC ($Na^+$-form column, 0.8 ml/min, 0.003 M $Na_2SO_4$, 85° C.).

Figure 4:
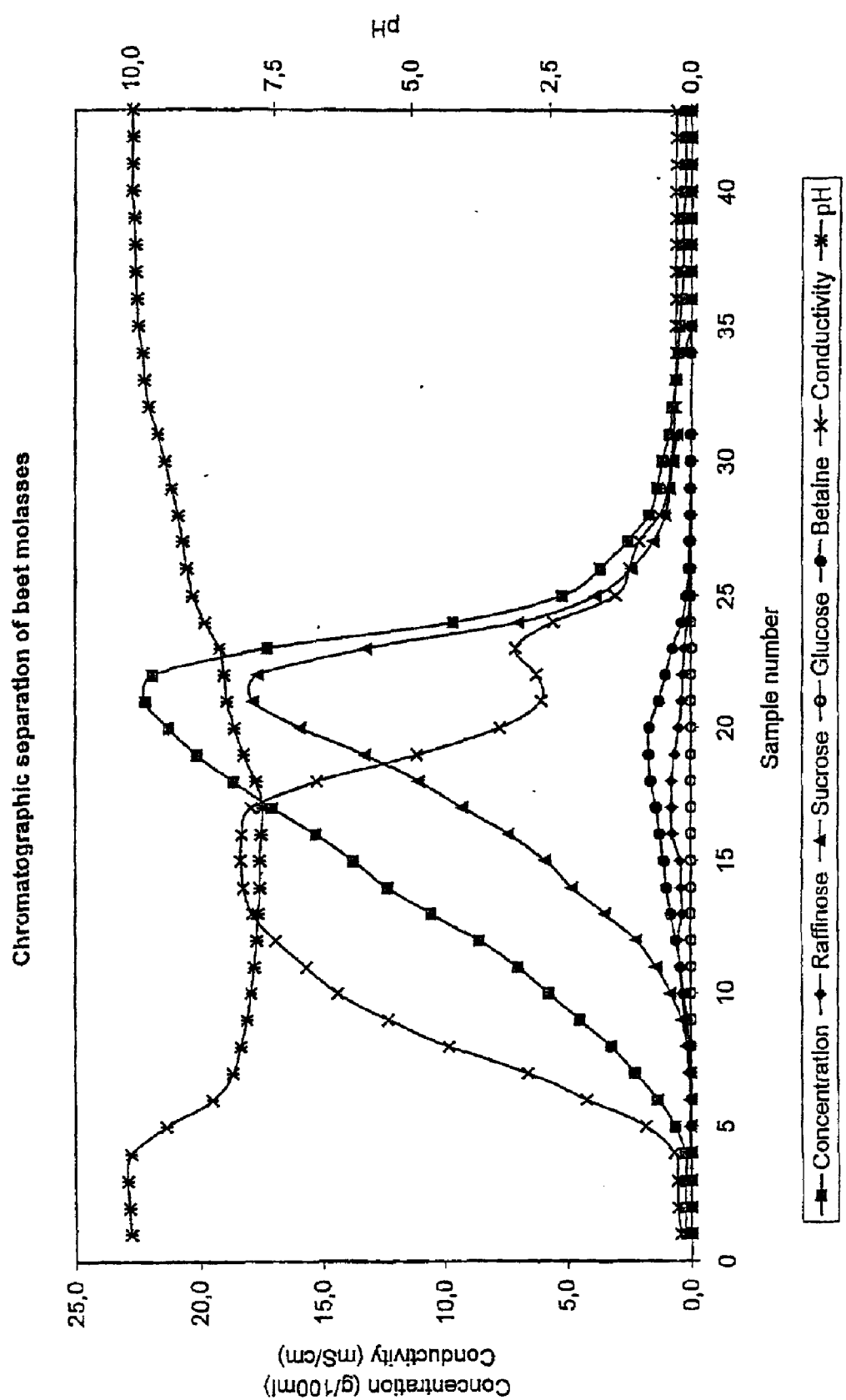
FIG. 4 is a graphical presentation of the elution profiles and pH according to Example 4.

Salts eluted out of the column first. Sucrose and betaine are eluted at the same retention time and overlapped with the salts to some extent. α-amino acids eluted mainly at the back slope of the profile. The pH of the effluent, the solution coming out of the column is from 8 to 11. The results are shown graphically in FIG. 4. Table 1 shows the amino acid concentration of samples 21 to 39.

TABLE 1

Amino acid concentration of the samples

| Sample number | RDS g/100 g | Amino acids % on DS | Amino acids g/100 g |
|---|---|---|---|
| 21 | 20.54 | 1.8 | 0.370 |
| 23 | 16.36 | 3.1 | 0.507 |
| 25 | 5.09 | 8.5 | 0.433 |
| 26 | 3.58 | 13.0 | 0.465 |
| 27 | 2.47 | 16.5 | 0.408 |
| 29 | 1.28 | 4.9 | 0.063 |

EXAMPLE 5

Chromatographic SMB Separation of Beet Molasses with Weakly Acid Cation Exchange Resin The test equipment included four columns connected in series, feed pump, recycling pumps, eluant water pump as well as feed inlet valves and product outlet valves for the various process streams. The height of each column was 3 m and each column had a diameter of 0.2 m. The columns were packed with a weakly acid gel type cation exchange resin in $Na^+$ form. The mean bead size was 0.23 mm and DVB content 6.0%.

The feed material was beet molasses. The molasses was diluted to 45 Bx and carbonated with sodium carbonate (1.5% on DS basis, temperature 60° C., 3 h reaction time). The carbonated solution was filtered with Seitz pressure filter using Kenite 300 as a filtering aid (precoat 1 kg/m$^2$, bodyfeed 0.5% on DS basis). The feed dry substance concentration was adjusted to 56 g/100 ml. The composition is set forth in the table below, whereby the percentages are given on a dry substance weight basis.

TABLE 2

Composition of feed

| DS concentration, g/100 ml | 56.0 |
|---|---|
| Sucrose, % on DS | 57.0 |
| Betaine, % on DS | 6.6 |
| Amino acids, % on DS | 3.3 |
| Others, % on DS | 33.1 |

The fractionation was performed by way of a 6-step sequence as set forth below. The feed was used at a temperature of 80° C. and water was used as an eluant.

Step 1: 8.1 l of feed solution were pumped into the first column at a flow rate of 90 l/h and a sucrose fraction was collected from column 4.

Step 2: 19 l of feed solution were pumped to the first column at a flow rate of 90 l/h and a residual fraction (raffinate fraction) was collected from column 1. Simultaneously 19 l of water were pumped to column 2 at a flow rate of 90 l/h and a residual fraction was collected from column 2. Simultaneously 26 l of water were pumped to column 4 at a flow rate of 123 l/h and a sucrose fraction was collected from column 4.

Step 3: 10.8 l was circulated at a flow rate of 120 l/h.

Step 4: 20.2 l of water was pumped to the first column at a flow rate of 20 l/h and a amino acid fraction was collected from column 4.

Step 5: 18.8 l water was pumped to the first column at a flow rate of 120 l/h and a residual fraction was collected from column 2. Simultaneously 18.9 l water was pumped to column 3 at a flow rate of 12 l/h and a residual fraction was collected from column 4.

Step 6: 23.0 l were circulated at a flow rate of 120 l/h.

After equilibration of the system, the following fractions were drawn from the system: residual fractions from each column, sucrose containing fraction from column 4 and amino acid containing fraction from column 4. All residual fractions were combined. The results are set forth in the table below.

TABLE 3

Result of the fractionation

| Fractions | Sucrose | Combined residual | Amino acid |
|---|---|---|---|
| Volume, l | 33.9 | 75.7 | 20.3 |
| DS concentration, g/100 ml | 28.5 | 6.5 | 3.0 |
| Sucrose, % on DS | 83.6 | 9.3 | 21.5 |
| Betaine, % on DS | 9.7 | 1.5 | 0.0 |
| Amino acids, % on DS | 1.7 | 3.2 | 29.3 |
| Others, % on DS | 5.0 | 86.0 | 49.2 |

EXAMPLE 6

Betaine Crystallization

The betaine containing feed liquid was added to a 400-liter boiling crystallizer. The evaporation was started. First spontaneous crystals were seen at DS of about 79%, at a temperature of 99° C. After spontaneous seeding, the boiling crystallization was continued for 3 hours at a temperature of about 100° C. and new feed liquid was added continuously into the boiling crystallizer. A 400-liter batch of the mass obtained by boiling crystallization (DS of mass 87%) was discharged. The mass was centrifuged and betaine anhydrous product was dried.

EXAMPLE 7

Inositol Crystallization

The inositol containing feed liquid was added to a 400-liter boiling crystallizer. The evaporation was started at a temperature of 50° C. The boiling liquid was seeded with 5 ml seed suspension (150 g milled inositol in 500 ml isopropanol) at DS of 42%, at temperature of 50° C. After seeding, the boiling crystallization was continued for 2 hours at a temperature of 50° C. and new feed liquid was added continuously into the boiling crystallizer. A 400-liter batch of the mass obtained by boiling crystallization (DS of mass 44%) was discharged. The mass was centrifuged and crystals dried.

What is claimed is:

1. A method comprising a multistep process for recovering one or more products from a process solution containing one or more product components selected from the group consisting of betaine, erythritol, inositol, sucrose, mannitol, glycerol, amino acids and mixtures thereof by using chromatographic separation comprising at least one step, where a weak acid cation exchange resin is used for the chromatographic separation.

2. The method of claim 1 wherein the solution to be treated is a sugar beet derived process solution.

3. The method of claim 2 wherein the sugar beet derived process solution is vinasse, molasses or betaine molasses.

4. The method of claim 1 wherein the product is betaine.

5. The method of claim 1 wherein the product is inositol.

6. The method of claim 1 wherein the product is mannitol.

7. The method of claim 1 wherein the chromatographic separation comprises at least one column or a part of a column, which contains a weak acid cation exchange resin.

8. The method of claim 1 wherein the chromatographic separation comprises at least one column or a part of a column, which contains a strong acid cation exchange resin.

9. The method of claim 1 wherein the weak acid cation exchange resin is an acrylic resin.

10. The method of claim 9 wherein the acrylic resin is derived from the group consisting of methyl acrylate, ethyl acrylate, butyl acrylate, methyl methacrylate, acrylonitrile, acrylic acids and mixtures thereof.

11. The method of claim 10, wherein the cation of said weak cation exchange resin is selected from the group consisting of Na+, K+, H+, Mg2+ and Ca2+.

12. The method of claim 11 wherein the cation of said weak cation exchange resin is in Na+ and/or K+ form.

13. The method of claim 9 wherein the resin is crosslinked with divinyl benzene.

14. The method of claim 13 wherein the crosslinking degree of the resin is 3 to 8% by weight.

15. The method of claim 1 wherein the eluant used in the chromatographic separation is water.

16. The method of claim 1 comprising feeding the process solution to a first chromatographic column containing a weak acid cation exchange resin and then feeding a fraction from the first chromatographic column to a second chromatographic column containing a strong acid cation exchange resin.

17. The method of claim 1 comprising feeding the process solution to a first chromatographic column containing a strong acid cation exchange resin and then feeding a fraction from the first chromatographic column to a second chromatographic column containing a weak acid cation exchange resin.

18. The method of claim 17 comprising feeding a fraction from the second chromatographic column to a third chromatographic column containing a weak acid cation exchange resin and feeding a fraction from the third chromatographic column to a fourth chromatographic column containing a weak acid cation exchange resin.

19. The method of claim 16 wherein a concentration or filtration unit is arranged between said first and second chromatographic columns.

20. The method of claim 16 wherein, prior to feeding the fraction to a said second chromatographic column, said fraction is concentrated by evaporation.

21. The method of claim 17 wherein, prior to feeding the fraction to said second chromatographic column, said fraction is concentrated by evaporation.

22. The method of claim 18 wherein, prior to feeding the fraction to a further chromatographic column, said fraction is concentrated by evaporation.

23. The method of claim 19 wherein, prior to feeding the fraction from one chromatographic column to another, said fraction is concentrated by evaporation.

24. The method of claim 1 further comprising one or more of the steps of crystallization, ion exchange or precipitation.

25. The method of claim 1 wherein the temperature of the eluent used in the chromatographic separation is between 10° C. and 95° C.

26. The method of claim 25 wherein the temperature of the eluent is between 65° C. and 95° C.

27. The method of claim 1 wherein the particle size of the weak acid cation exchange resin is 10 $\mu$m to 2000 $\mu$m.

28. The method of claim 27 wherein the particle size of the weak acid cation exchange resin is 100 $\mu$m to 400 $\mu$m.

29. The method of claim 1 wherein a feed solution has a pH of from 6 to 11.

30. The method of claim 29 wherein the feed solution has a pH of from 9 to 11.

31. The method of claim 1 wherein the chromatographic separation is a batch process.

32. The method of claim 1 wherein the chromatographic separation is a simulated moving bed process.

33. The method of claim 32 wherein the simulated moving bed process is a sequential process.

34. The method of claim 32 wherein the simulated moving bed process is a continuous process.

35. The method of claim 33 where the weak acid cation exchange resin is used in at least one column.

36. The method of claim 34 where the weak acid cation exchange resin is used in at least one column.

37. The method of claim 33 wherein a strong acid cation exchange resin is used in at least one column.

38. The method of claim 34 where a strong acid cation exchange resin is used in at least one column.

39. The method of claim 1 comprising recovering betaine from a first and inositol, erythritol and mannitol from a second chromatographic column.

40. The method of claim 1 further comprising isolating betaine, inositol, erythritol, mannitol and glycerol by crystallization.

41. The method of claim 1 comprising recovering a sucrose fraction.

42. The method of claim 41 comprising separating amino acids and/or betaine from the sucrose fraction.

43. The method of claim 17 wherein a concentration or filtration unit is arranged between chromatographic columns.

44. The method of claim 18 wherein a concentration or filtration unit is arranged between chromatographic columns.

* * * * *

UNITED STATES PATENT AND TRADEMARK OFFICE
CERTIFICATE OF CORRECTION

PATENT NO. : 6,770,757 B2
DATED : August 3, 2004
INVENTOR(S) : Hannu Paananen et al.

It is certified that error appears in the above-identified patent and that said Letters Patent is hereby corrected as shown below:

Title page,
Item [30], "(FI) 2001-2150" should read -- FI 2000-2150 --

Signed and Sealed this

Fourth Day of January, 2005

JON W. DUDAS
*Director of the United States Patent and Trademark Office*